United States Patent [19]

Tsuru et al.

[11] Patent Number: 5,843,421
[45] Date of Patent: Dec. 1, 1998

[54] HAIR TONIC

[75] Inventors: Tatsuya Tsuru, Iwaki; Katsuhiro Ishimi, Chigasaki; Koh Kusama; Yasuo Fujimoto, both of Tokyo; Yoshiyuki Ichinohe, Kamakura, all of Japan

[73] Assignee: Toyotomi Co., Ltd., Fukushima-ken, Japan

[21] Appl. No.: 622,018

[22] Filed: Mar. 26, 1996

Related U.S. Application Data

[63] Continuation-in-part of Ser. No. 465,796, Jun. 6, 1995, abandoned, which is a continuation of Ser. No. 87,056, Jul. 7, 1993, abandoned.

[30] Foreign Application Priority Data

Jul. 8, 1992 [JP] Japan ..................................... 4-181313

[51] Int. Cl.⁶ ...................................................... A61K 7/06
[52] U.S. Cl. ............................................ 424/74; 424/195.1
[58] Field of Search ..................................... 424/74, 195.1

[56] References Cited

U.S. PATENT DOCUMENTS 4,769,231  9/1988  Ogura et al. .............................. 424/74

OTHER PUBLICATIONS

Young, David A., Flavonoid Chemistry and the Phylogenetic Relationships of the Julianiaceae, Systematic Botany, vol. 1, No. 2, issued Nov. 30, 1976, pp. 149–162.

*Primary Examiner*—Robert H. Harrison
*Attorney, Agent, or Firm*—Finnegan, Henderson, Farabow, Garrett & Dunner, L.L.P.

[57] ABSTRACT

A hair tonic containing an extract of a plant of the family Julianiaceae such as *Juliania adstringens, Amphipterygium adstringens* or *Orthopterygium huancuy* as an active ingredient. The bark of the plant is used as it is or in pulverized or ground form and extracted by using a solvent which does the human body no harm. The extract is so added to the hair tonic that its content on dry basis becomes 2.5~25% (w/w) to the whole quantity of the hair tonic.

12 Claims, No Drawings

HAIR TONIC

CROSS-REFERENCE TO RELATED APPLICATION

The present invention is a continuation-in-part of U.S. patent application Ser. No. 08/465,796 filed on Jun. 6, 1995, now abandoned, which is a continuation of U.S. patent application Ser. No. 08/087,056 filed on Jul. 7, 1993, abandoned.

FIELD OF THE INVENTION

This invention relates to a hair tonic containing an extract of a plant as an active ingredient.

BACKGROUND OF THE INVENTION

It has been told as Indian's transmission that plants of the family Julianiaceae are effective for gastroentric disorders and shows cancerocidal action and the like by boiling down the bark of the plants and ingesting the resulting liquid.

However, it has not been known that an extract of a plant of the family Julianiaceae show the hair tonic effect.

SUMMARY OF THE INVENTION

This invention purposes to provide a truly effective hair tonic containing an extract of a plant as an active ingredient.

According to the present invention, a truly effective hair tonic containing an extract of a plant as an active ingredient can be obtained.

The present inventors made an intensive study in order to develop a truly effective hair tonic. As the result, they found that an extract of a plant of the family Julianiaceae had a very effective hair tonic action, based on which they completed the present invention.

That is, the feature of the present hair tonic lies in containing an extract of a plant of the family Julianiaceae as an active ingredient.

DETAILED DESCRIPTION OF THE INVENTION

As preferable examples of a plant of the family Julianiaceae to be used as a material in the present invention, *Juliania adstringens* (CUACHALALATE), *Amphipterygium adstringens* or *Orthopterygium huancuy* can be enumerated. Particularly, the barks of these plants are preferable.

As examples of an extraction solvent, water: alcohols, e.g., methanol, ethanol, propanol, butanol; ethers, e.g., ethyl ether, dioxane; ketones, e.g., acetone; etc. can be enumerated. In case of using an extract as a dried product after once making free from a solvent, any of the abovementioned solvents can be used independently or as a mixture. On the other hand, in case of using an extract in such a state as dissolved in a solvent, it is necessary to use such a solvent as does not show a harmful action to the human body and thus it is preferred to use water, ethanol or their mixture.

In the present invention, alcohols are preferably used as the extraction solvent. The alcohols can be used singly or as their mixture. The alcohol used singly is preferably methanol or ethanol, particularly ethanol. The alcohols used as a mixture are preferably a combination of methanol and ethanol. In case a combination of methanol and ethanol is used, it is preferred to carry out extraction first with methanol and then with ethanol.

It is particularly preferred to carry out extraction with a nonpolar solvent and subsequent extraction of the residues with alcohols. This preceding nonpolar-solvent extraction permits removal of unnecessary components and efficient alcohol extraction because the active ingredient required in the present invention is not dissolved in a nonpolar solvent but dissolved in alcohols.

Preferable examples of such nonpolar solvents are n-hexane, cyclohexane, n-heptane, benzene, carbon disulfide and carbon tetrasulfide, among which n-hexane, cyclohexane and n-heptane are particularly preferable.

At the time of extraction, a plant of the family Julianiaceae, preferably the bark of the plant may be not only used as it is but also pulverized or around so as to strengthen its contact with a solvent.

There is no particular restriction to the ratio of a plant of the family Julianiaceae to a solvent. However, it is preferably 5~25 L of a solvent per kg of a plant of the family Julianiaceae.

The extraction temperature is preferably room temperature or within the range of the boiling point of a solvent under atmospheric pressure. The extraction time, though it depends upon the extraction temperature and the like, is preferably 1 hour to 1 day.

Although there is no particular restriction to the mixing ratio of an extract of a plant of of the family Julianiaceae because the extract show no toxicity to the human body, it is preferred that the quantity of the extract (on dry basis) is 2.5~25% (w/w) to the whole quantity of the present hair tonic.

As a base to be used for the present hair tonic, any base commonly used for cosmetic compositions can be used. For example, water; monovalent alcohols such as ethanol, etc.; polyvalent alcohols such as glycerine, ethylene glycol, etc.; fats and oils; surfactants; etc. can be used.

The present hair tonic can contain other ingredients having hair tonic actions and ingredients which are used for hair tonics and hair dressing preparations as far as its effect may not be damaged. As examples of these ingredients, hormones, vitamins, amino acids, crude drug extracts, pigments, resolcin, menthol, wetting agents, fragrances, etc. can be enumerated.

The present hair tonic show a strong hair tonic effect when it is applied to the human scalp or the animal skin.

As aforementioned, the present hair tonic has been ingested for a long time and thus has no problem of safety to humans and animals.

EXAMPLES

Hereinafter, the present invention will be described more specifically, referring to examples. However, the scope of the present invention is nowise restricted to the examples.

Example 1 Preparation of Extract 10 kg of the bark of *Juliania adstringens* (CUACHALALATE) and 200 g of swertia herb were put into 200 L of tap water and boiled at 100° C. for 4 hours. The supernatant was filtered to obtain 100 L of an extract. 100 L of this extract was mixed with 5 L of ethanol and 5 kg of magnesium aluminium silicate to obtain the present hair tonic.

Incidentally, the above extract was dried to give 98 g of dry product per 420 g of the bark.

Example 2 Preparation of Extract 500 g of the bark of *Juliania adstringens* (CUACHALALATE) was put into 5 L of tap water and boiled at 100° C. for 4 hours. Then, the supernatant was filtered to obtain 2.5 L of an extract.

Example 3 Preparation of Extract 1 kg of the bark of *Juliania adstringens* (CUACHALALATE) and 20 g of swertia herb were put into 20 L of tap water and boiled at 100° C. for 4 hours. The supernatant was filtered to obtain 10 L of an extract.

Example 4 Preparation of Extract 200 g (on dry basis) of the bark and roots of *Juliania adstringens* (CUACHALALATE) were extracted 3 times with 500 ml n-hexane under heating at 70° C. 6–7 g of the extract was used for preparation of a hair tonic, which was then applied to subjects. The result indicated that it had no effect on hair restoration.

The residues of the bark and roots remaining after n-hexane extraction were extracted 3 times with 500 ml methanol under heating at 65° C. The reddish brown solution thus obtained was concentrated under reduced pressure to give 40–45 g viscous substance partially containing crystalline precipitates.

Example 5 Prescription Example

Hereinafter, prescription examples of the present hair tonic are given.

(1) Hair Tonic

Prescription A

Extract obtained in Example 2 95% (w/w)

Isopropyl alcohol 5% (w/w)

Prescription B

Extract obtained in Example 3 95% (w/w)

Ethanol 5% (w/w)

Prescription C

Extract obtained in Example 4 95% (w/w)

Isopropyl alcohol 5% (w/w)

(2) Hair Cream

Extract obtained in Example 3 95% (w/w)

Magnesium aluminium Silicate 3% (w/w)

Gel obtained by mixing
the above ingredient 95% (w/w)

Isopropyl alcohol 5% (w/w)

Example 6 Application Example

The hair tonic prescribed in Example 5 (Prescription A,B) was applied to subjects. The results were given in Table 1.

TABLE 1

| Subject No. | Rank | Prescription | Report on Use (Effect) |
|---|---|---|---|
| 1 | A | A | In 1 month, the first hair grew overall. In 6 months, a large number of downy hairs grew. In 1~2 years, parts where short hairs grew and became long have spread gradually. |
| 2 | C | A | In 1 week, the effect was shown. In 6 month, downy hair grew in about half of the hair-lost part. In 1 year, downy hair grew in the whole hair-lost part. The downy hair, though its growth is slower than that of other hairs, came to grow long, stiff and thick. |
| 3 | A | A | Downy hair became long, stiff and straight, which the subject himself was conscious of in year. Hair, which fell down in the state of downy hair at the beginning, has come to grow thick, long and straight. |
| 4 | A | A | After 1 month, the subject himself reported that the effect was shown. |
| 5 | C | A | Two subjects were tested, and the both reported that effects were shown. |
| 6 | A | A | In 6 months, downy hair grew densely and black hair came to grow in the front central part. In 1 year, long hair increased considerably and thus the subject came to comb his hair. |
| 7 | A | A | At 1-week intervals, the growth of hair was photographed. In about 2 months, the effect was recognized. |
| 8 | B | A | In 1 year, black hair came to grow among gray hair and the hair thinness became inconspicuous. The rank improved from B to C. |
| 9 | A | A | Black hair came to grow. The subject himself reported that a significant effect was shown. The effect became prominent when the subject had his hair cropped short. |
| 10 | B | B | In 1 month, hair falling became reduced and hair became stiff. In 1 year, the rank was improved from B~C |
| 11 | B | A | Falling of 15~20 hairs per day was discontinued, and black hair came to grow. |
| 12 | B | B | The subject himself reported that the effect was shown in 1 week. |
| 13 | C | B | Hair falling was discontinued and alopecia areata was cured. |
| 14 | A | B | In 2 months, black hair came to grow and a circular on the posterior vertex became small considerably. |
| 15 | A | B | White hair grew in the hairless part, and hair came not to hang down forwards when it was parted. |
| 16 | B | B | After 2 months, the subject himself reported that the effect was shown. |
| 17 | A | B | The subject himself reported that loss of hair discontinued in 1 week and hair became black. |
| 18 | C | B | In 1 month, black hair came to grow. Thereafter, the thinness of hair became inconspicuous considerably. |
| 19 | B | B | In 3 weeks, the growth of hair was confirmed. |
| 20 | C | B | The subject himself reported that hair became stiff and loss of hair discontinued. |

Rank A: A person who can be told as bald at a glance.
Rank B: A person having thin hair even letting his hair grow long.
Rank C: A person who cannot be found to have thin hair when letting his hair grow long.

Example 7 Application Example

The hair cream prepared in Example 5 (Prescription A,B) was applied to subjects. The results were given in Table 2.

TABLE 2

| Subject No. | Rank | Report on Use (Effect) |
|---|---|---|
| 1 | B | Within 3 months, downy hair grew, which then became streaked with black hair in places and came to grow long. |
| 2 | B | Within 3 months, loss of hair became discontinued and hairs became stiff. |

TABLE 2-continued

| Subject No. | Rank | Report on Use (Effect) |
|---|---|---|
| 3 | B | In about 1 week, loss of hair became discontinued and downy hair came to grow. |
| 4 | C | Within 3 months, loss of hair became discontinued. |
| 5 | A | In about 10 days, short black hair came to grow overall. |

Rank A: A person who can be told as bald at a glance.
Rank B: A person having thin hair even letting his hair grow long.
Rank C: A person who cannot be found to have thin hair when letting his hair grow long.

Example 8 Application Example

The hair tonic prescribed in Example 5 (Prescription C) was applied to subjects. The results were given in Table 3.

TABLE 3

G cases

| Patient's initials | Sex | Age | Date of first medical examination | Name of disease | Duration of disease | Date of medical examination | Photograph | Frequency of application | Findings Fallen hair | Hair restoration | Dandruff | Degree of improvement | Side effects | Degree of usefulness | Feeling in use | Examinee's opinion Feeling of effectiveness | Continuation of use | Other opinion |
|---|---|---|---|---|---|---|---|---|---|---|---|---|---|---|---|---|---|---|
| K. K | male | 34 | Dec. 10, 1902 | male alopecia | 6 years and 0 month | 12/10 | present | — | moderate | — | slight | significantly improved | absent | very useful | good | good | present | |
| | | | | | | 1/6 | absent | 2–3 times/day | unchanged | | unchanged | | | | | | | |
| | | | | | | 2/5 | absent | 2–3 times/day | decreased | | unchanged | | | | | | | |
| | | | | | | 3/3 | present | 2–3 times/day | decreased | | unchanged | | | | | | | |
| M. M | female | 67 | Nov. 24, 1992 | senile alopecia | 5 years and 0 month | 11/24 | present | — | moderate | — | slight | improved | absent | useful | good | good | present | |
| | | | | | | 12/22 | absent | 2–3 times/day | unchanged | absent | unchanged | | | | | | | |
| | | | | | | 1/22 | absent | 2–3 times/day | decreased | | unchanged | | | | | | | |
| | | | | | | 2/15 | present | 2–3 times/day | decreased | | unchanged | | | | | | | |
| T. M | male | 46 | Dec. 4, 1991 | male alopecia | 3 years and 6 months | 12/16 | present | — | slight | — | moderate | significantly improved | absent | very useful | not good | slightly good | absent | Clothes stain The stain can not wash out. |
| | | | | | | 1/13 | absent | 2–3 times/day | unchanged | absent | unchanged | | | | | | | |
| | | | | | | 2/12 | absent | 2–3 times/day | unchanged | | unchanged | | | | | | | |
| | | | | | | 2/6 | present | 2–3 times/day | increased | absent | unchanged | | | | | | | |
| M. S | male | 46 | Nov. 17, 1992 | male alopecia | 6 years and 0 month | 11/17 | present | — | moderate | — | moderate | improved | absent | useful | good | slightly goodness | present | |

TABLE 3-continued

G cases

| Patient's initials | Sex | Age | Date of first medical examination | Name of disease | Duration of disease | Date of medical examination | Photograph | Frequency of application | Fallen hair | Findings Hair restoration | Dandruff | Degree of improvement | Side effects | Feeling of usefulness | Feeling in use | Examinee's opinion Feeling of effectiveness | Continuation of use | Other opinion |
|---|---|---|---|---|---|---|---|---|---|---|---|---|---|---|---|---|---|---|
| | | | | | | 1/16 | absent | 2–3 times/day | decreased | | | unchanged | | | | | | |
| Y. Y | male | 36 | Jun. 24, 1992 | male alopecia | 16 years and 0 month | 12/8 | present | — | moderate | — | slight | unchanged | absent | not definite | not definite | not good | absent | |
| | | | | | | 2/16 | absent | 2–3 times/day | unchanged | absent | | unchanged | | | | | | |
| | | | | | | 3/3 | present | 2–3 times/day | unchanged | absent | | unchanged | | | | | | |
| F. K | female | 79 | Dec. 4, 1982 | senile alopecia | 4 years and 1 month | 12/4 | present | — | moderate | — | slight | improved | absent | useful | not definite | unnoticed | present | The color should be more pale. |
| | | | | | | 2/12 | absent | 2–3 times/day | unchanged | | | unchanged | | | | | | |
| | | | | | | 2/13 | present | 2–3 times/day | decreased | absent | | unchanged | | | | | | |

NOTE:
(1) In the item "Degree of improvement", the term "unchanged" means that the disease is stopped.
(2) The data are obtained in a study in Kochi Nisseki Hospital (Kochi Red Cross Hospital) made by Professor Kimana (Toleushima University) and sponsored by Shionogi Pharmaceutical Company.

What is claimed is:

1. A method of treatment of hair loss, which comprises administering to a person a hair tonic comprising an effective amount of an extract of a plant of the family *Juliania adstringens*.

2. A method according to claim 1, wherein the hair tonic is applied to a human scalp.

3. A method according to claim 1, wherein the hair tonic is applied to an animal skin.

4. A method according to claim 1 wherein the hair tonic reduces hair loss.

5. A method according to claim 1, wherein the extract was obtained by extraction with a solvent selected from the group consisting of water, an alcohol, an ether, and a ketone.

6. A method according to claim 1, wherein the extract is obtained by extraction with an alcohol.

7. A method according to claim 6, wherein the alcohol is methanol and/or ethanol.

8. A method according to claim 6, wherein the alcohol extract is an extract obtained by extraction with methanol and then with ethanol.

9. A method according to claim 6, wherein the alcohol extract is an extract obtained by extraction, with an alcohol, of residues remaining after extraction with a nonpolar solvent.

10. A method according to claim 1, wherein the extraction solvent is water.

11. A method according to claim 1, wherein the hair tonic contains, on a dry basis, from 2.5~25% by weight of the extract.

12. A method according to claim 1, wherein the hair tonic increases hair growth.

* * * * *